United States Patent [19]

Hayashi

[11] Patent Number: 5,077,393

[45] Date of Patent: Dec. 31, 1991

[54] METHOD FOR PRODUCING VITRONECTIN

[75] Inventor: Masao Hayashi, Tokyo, Japan

[73] Assignee: Research Development Corporation of Japan, Tokyo, Japan

[21] Appl. No.: 171,645

[22] Filed: Mar. 22, 1988

[30] Foreign Application Priority Data

May 25, 1987 [JP] Japan .................................. 62-125834

[51] Int. Cl.$^5$ .............................................. C07K 3/20
[52] U.S. Cl. .................................... 530/413; 435/101; 435/103; 530/350; 530/380; 530/395; 530/412; 530/415; 530/417; 530/419; 935/9
[58] Field of Search ............... 530/350, 380, 395, 412, 530/415, 417, 419, 413; 435/101, 103; 935/9

[56] References Cited

PUBLICATIONS

Suzuki et al.; Journal of Biological Chemistry; Domien Structure of Ultronectin; pp. 15307–15314 (1984).

B. Dahlback et al., Biochemistry, vol. 24, No. 9, pp. 2368–2374 (1985).
E. G. Hayman et al., Proc. Natl. Acad. Sci. U.S.A., vol. 80, pp. 4003–4007 (1983).
Takao Akama et al., J. Biochem., vol. 100, No. 5, pp. 1343–1351 (1986).
D. W. Barnes et al., The Journal of Biological Chemistry, vol. 258, No. 20, pp. 12548–12552 (1983).
Masao Hayashi et al., J. Biochem., vol. 98, No. 4, pp. 1135–1138 (1985).

Primary Examiner—Robert A. Wax
Assistant Examiner—Ardin Marschel
Attorney, Agent, or Firm—Sherman and Shalloway

[57] ABSTRACT

This invention deals with a simple and efficient method for producing vitronectin from biological materials which include vitronectin. More specifically, this invention deals with a method for producing vitronectin by binding vitronectin in biological materials to immobilized glycosaminoglycans in the presence of protein denaturing agent, especially urea.

8 Claims, 2 Drawing Sheets ered with ca. 8% of recovery (Barnes and Silnutzer; J.Biol.Chem. vol.258, pp.12548-12552, 1983).

METHOD FOR PRODUCING VITRONECTIN

FIELD OF THE INVENTION

Vitronectin is a glycoprotein in animal body fluid and tissues. Its molecular weight is 60,000-80,000. Vitronectin is also called as serum spreading factor, S-protein, or epibolin (Masao Hayashi; Kagaku to Seibutsu, vol.24, pp.303-313, 1986).

This invention deals with a simple and efficient method for producing vitronectin. More specifically, this invention deals with a method for producing vitronectin by binding vitronectin in biological materials to immobilized glycosaminoglycans.

DESCRIPTION OF THE PRIOR ART

Up till now, the following three methods, which use human plasma/serum as starting materials, are known as methods for producing vitronectin.

Method 1. Four different columns are combined. These are glass bead, concanavalin A-Sepharose, DEAE-agarose, and heparin-Sepharose columns. Vitronectin is produced from human plasma/serum with ca. 8% of recovery (Barnes and Silnutzer; J.Biol.Chem. vol.258, pp.12548-12552, 1983).

Method 2. Two columns of anti-human vitronectin monoclonal antibody and heparin-Sepharose are combined. The recovery is about 10-20% (Hayman et al.; Proc.Nat.Acad.Sci. USA vol.80, pp.4003-4007, 1983).

Method 3. This method consists of 5 processes. After 2 processes of fractionation, that is, absorption by barium citrate and fractionation by polyethylene glycol 4000, 3 columns of DEAE-cellulose, Blue Sepharose, and anti-albumin Sepharose are combined. Vitronectin is obtained with ca. 7% of recovery (Dahlbäck and Podack; Biochemistry vol.24, pp. 2368, 2374, 1985).

These methods involve the following problems. Method 1 is a complex of 4 different processes, time-consuming (usually about 1 month), and inefficient in recovery (ca. 8%). Method 2 involves the employment of monoclonal antibody. As the result, the method can be applied only to human materials, is too limited and expensive. Method 3 is a complex of 5 different steps, time-consuming (usually about 2 weeks), and inefficient in recovery (ca. 7%). Therefore, each method is unsatisfactory and not good enough for industrial use.

SUMMARY OF THE INVENTION

The purpose of the invention involves the production of vitronectin from biological materials simply, with low cost and efficiently. It also involves the production of vitronectin not only from human plasma but also from biological materials of other animal species. Another purpose of the invention is the production of vitronectin from different kinds of materials such as body fluid, tissues and so on.

These purposes can be reached by binding vitronectin in biological materials specifically to immobilized glycosaminoglycans in the presence of protein denaturing agent, especially urea.

The inventor has been studying vitronectin biochemically and cell biologically for a long time. He found that vitronectin changes its conformation by urea so that its binding activity to heparin, a glycosaminoglycans, increases (Hayashi et al.; J.Biochem. vol.98, pp.1135-1138, 1985). This finding has led the inventor to the invention.

DETAILED DESCRIPTION OF THE INVENTION

Figure 1:
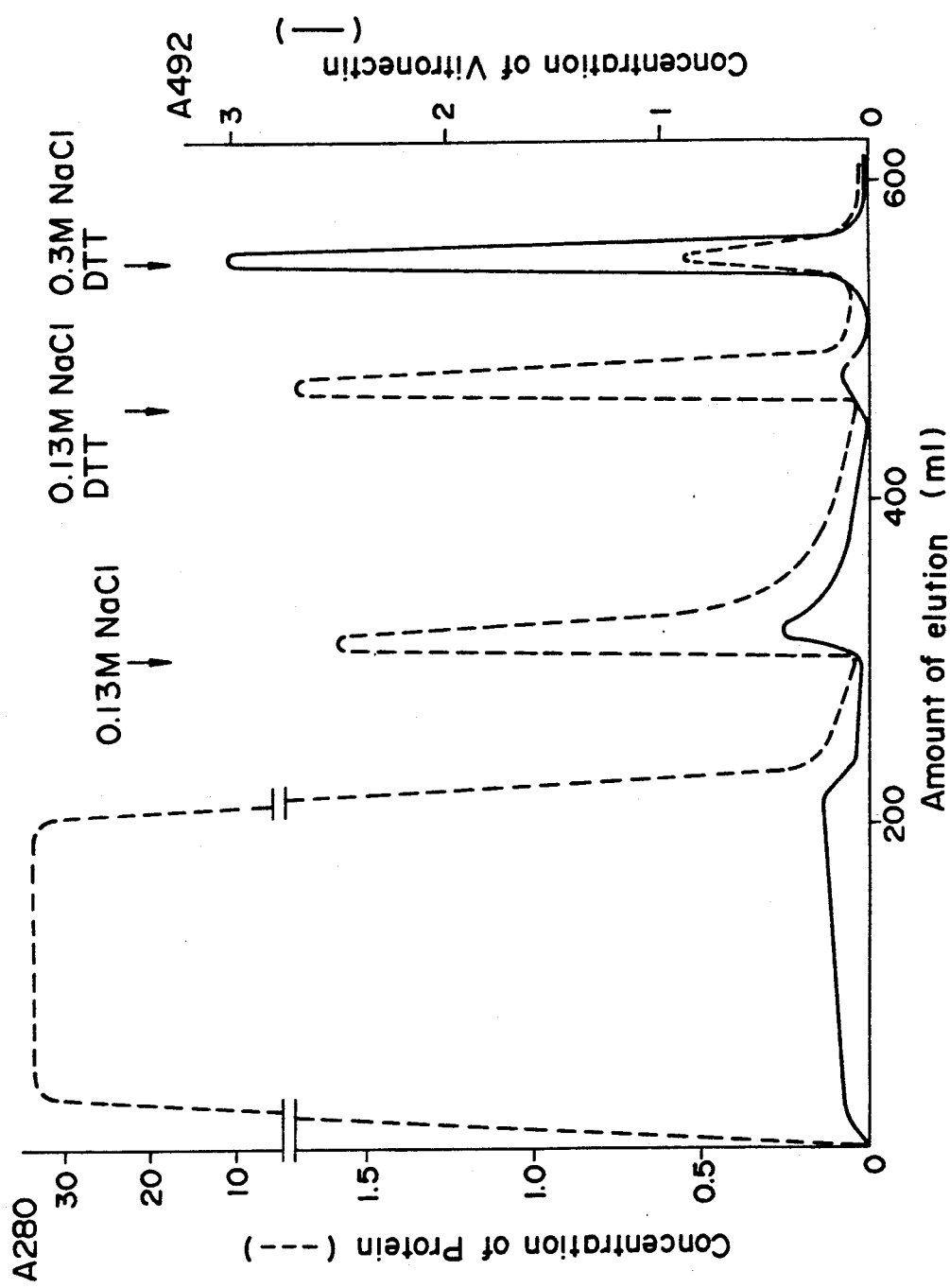
FIG. 1 shows an elution profile of heparin-Sepharose affinity chromatography. The preparation was obtained by the method in example 1. The broken line indicates protein concentrations determined from absorbance measurement at 280 nm. The solid line indicates the amount of vitronectin determined by enzyme-linked immunosorbent assay. The elution fractions between 535 ml and 560 ml constitute purified vitronectin.

Any biological materials which involve a small amount of vitronectin can be used as biological materials for the invention. Such biological materials involve body fluid including animal blood, plasma, serum and urine, tissues, organs, viscera, tissue-culture cells and tissue-culture medium. Human plasma and serum are best materials, but materials from other animal species can be also used. As protein denaturing agent, urea, guanidine-HCl or other agents can be used, nevertheless urea is especially desirable. As immobilized glycosaminoglycans, heparin-Sepharose, heparin sulfate-Sepharose, chondroitin sulfuric acid-Sepharose and dermatan sulfate-Sepharose carriers can be used. Agarose and other carriers can be substituted for the above Sepharose. Heparin-Sepharose carrier is most desirable.

Now, the invention is described in detail. Urea is so added to, as for example, plasma or serum of mammals that the final concentration of urea becomes 4-8M. The plasma/serum is mixed with glycosaminoglycan binding carrier such as heparin-Sepharose carrier. Vitronectin in plasma or serum is specifically bounded to the glycosaminoglycan binding carrier. Substances which weren't bound are washed out. Then, bound vitronectin is eluted from the immobilized glycosaminoglycans. po The invention is characterized as a method for producing vitronectin which consists of only one process of the employment of immobilized glycosaminoglycans.

As mentioned above, Barnes et al. (J.Biol.Chem. vol.258, pp.12548-12552, 1983) and Hayman et al. (Proc.Nat.Acad.Sci. USA vol.80, pp.4003-4007, 1983) also reported methods which involved the employment of heparin-Sepharose. However, in their procedures, the employment of heparin-Sepharose constitutes only the last and subsidiary process which increases the degree of purification to 1.5-2-fold of the preceding step. In contrast, in the invention, the purity of vitronectin increases up to ca. 400-fold only by the employment of heparin-Sepharose, without other columns. This characterizes the invention.

The precise mechanism of the specific interaction between vitronectin and glycosaminoglycans shown in the invention is unknown. Based on the results reported by the inventor (Hayashi et al.; J.Biochem. vol.98, pp.1135-1138, 1985: Akama et al.; J.Biochem. vol.100, pp.1343-1351, 1986), the following mechanism is inferred. Vitronectin has one site on its polypeptide chain which binds to glycosaminoglycans. Under usual conditions, this site is hidden inside of the polypeptide chain, so that its binding activity is low. The treatment of vitronectin with 4-8M urea unfolds the complex of polypeptide chain so that the hidden binding site gets free to bind to glycosaminoglycans. In addition, other heparin binding proteins in materials such as plasma lose their heparin binding activity in the presence of urea. Therefore, the addition of urea is efficient to bind vitronectin to glycosaminoglycans specifically. Usually, heparin is employed as glycosaminoglycans because of its high activity and low price.

THE EFFECT OF THE INVENTION

The advantages of the invention which deals with a method for producing vitronectin are:
  The method consists of only one process of producing.
  It requires only a short time (usually 1-3 days).
  The recovery is high (15-40%).
  The cost is low.

In addition, starting materials are not limited to human plasma or serum. That is, the method of the invention can also be applied to biological materials which include vitronectin regardless of animal species. Moreover, the method can also be applied to every kind of biological materials which include vitronectin, such as body fluid, tissues and their fragments. In short, the invention has the great advantages of the prior methods in economy of equipments, of time and in expenditure on industrializing. The invention has advantages in the range of starting materials, too. By coating vitronectin, the product of the invention, to cell culture plates, adhesion and spreading of different kinds of cells and bacteria can be controlled. The same effect can be achieved by adding vitronectin to cell culture medium. Vitronectin can also be used as cell adhesion agent for artificial blood vessels, artificial skins, contact lenses, artificial viscera, biosensors, biochips, electronic devices with biological function and so on. In short, vitronectin basically can be used as adhesion agent which binds cells and virus to every kind of materials. Regarding medical supplies, vitronectin can be used for diagnosis and treatment of different kinds of disease such as cancer, blood disease, collagen disease, which are thought to involve changes of vitronectin. Vitronectin can also be used for eye lotion, anti-infection agent, anti-inflammation agent, tissue repairing agent etc. Vitronectin may also be used for tooth-paste, cosmetics and so on.

EXAMPLES OF PRACTICE OF THE INVENTION

Several examples in which the invention is practiced follow. However, the invention is not limited to these examples.

EXAMPLE 1

Figure 2:
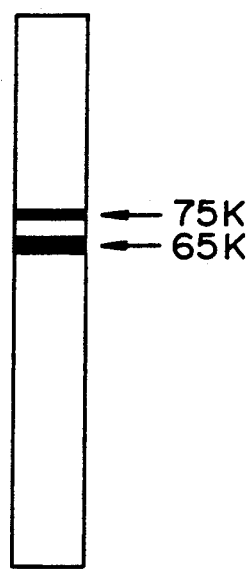
FIG. 2 shows the purity of vitronectin of example 1, determined by SDS-polyacrylamide gel electrophoresis. There are 2 bands (indicated by arrows) between molecular weight of 60,000 and 80,000. These 2 bands correspond to vitronectin. Contamination of any other proteins was not found.
Figure 3:
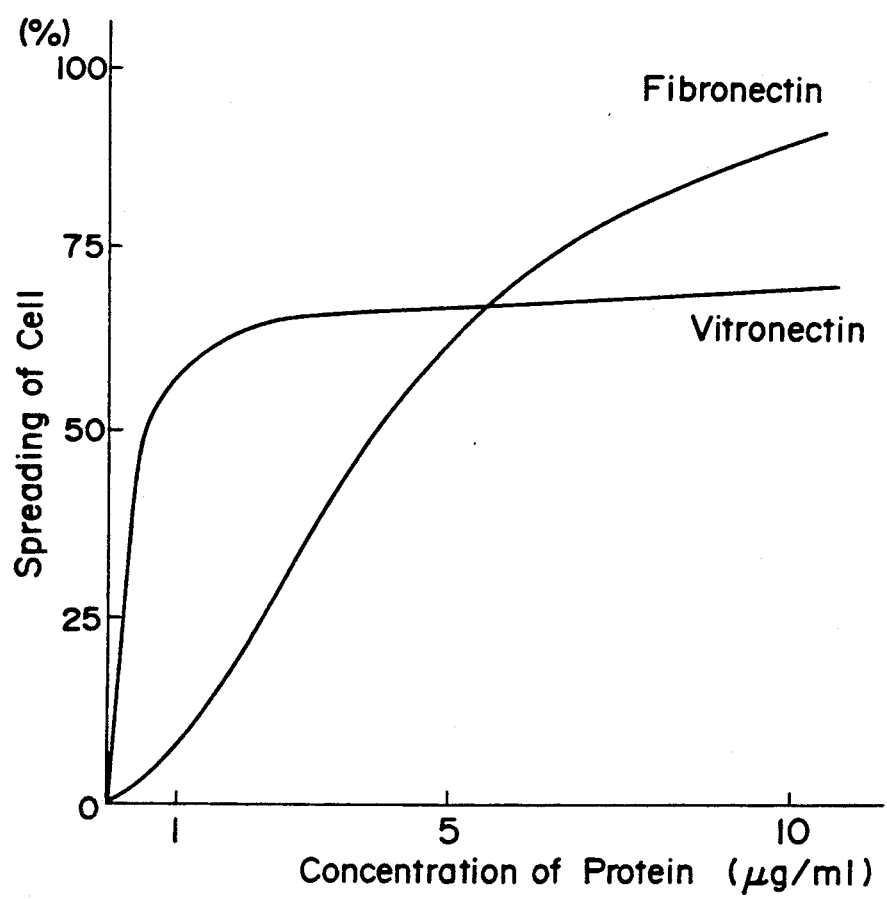
FIG. 3 shows the physiological activity of the purified vitronectin prepared by the method in example 1. The activity was determined as BHK cell-spreading activity. The preparation of vitronectin promotes the spreading of BHK cells around 1/50 of protein concentration which is known for fibronectin.

Ethanol is so added to 100 ml of human plasma at 4° C. that the final concentration of ethanol becomes 10%. Fibrinogen etc. are removed by centrifugation (10,000 rpm, 10 min.) at 4° C. The following procedures are performed at room temperature. Urea is added to the resulting liquid fraction for a final concentration of 8M urea. After 2 hr., the mixture is applied to 5 ml bed volume of heparin-Sepharose column. The column is washed with 10 column volumes of 8M urea, 5 mM EDTA, 10 mM phosphate buffer (pH 7.7). The column is washed again with 15 column volumes of 8M urea, 5 mM EDTA, 10 mM phosphate buffer containing 0.13M NaCl. Then the column is washed with 10 column volumes of 8M urea, 5 mM EDTA, 10 mM phosphate buffer containing 0.13M NaCl and 1 mM dithiothreitol. Vitronectin is subsequently eluted from the column with 10 column volumes of 8M urea, 5 mM EDTA, 10 mM phosphate buffer containing 0.3M NaCl, 1 mM dithiothreitol. FIG. 1 shows an example of elution profile. The starting material was human plasma. The amount of vitronectin was measured by the enzyme-linked immunosorbent assay, which uses rabbit anti-human vitronectin antibody. FIG. 2 shows the result of SDS-polyacrylamide gel electrophoresis, which indicates the purity of obtained vitronectin. Only 2 bands of ca. 60,000-80,000 in molecular weight appeared, which suggests that the vitronectin preparation has high purity. FIG. 3 shows that obtained vitronectin promotes adhesion and spreading of BHK cells (tissue-culture cells of hamster kidney) on cell culture plates. This effect of vitronectin is observed already at the protein concentration of 0.1 μg/ml.

EXAMPLE 2

The method of example 1 was modified as follows. Human serum was used instead of human plasma. Ethanol was not added. 10mM $MgCl_2$, 1 mM $CaCl_2$, 20 mM Tris-HCl buffer (pH 8.0) was employed instead of 5 mM EDTA, 10 mM phosphate buffer (pH 7.7).

EXAMPLE 3

The method of example 1 was modified as follows. The step of washing with 8M urea, 5 mM EDTA, 10 mM phosphate buffer containing 0.13M NaCl, 1 mM dithiothreitol was omitted. For elution, 0.21M NaCl, 8M urea, 5 mM EDTA, 10 mM phosphate buffer was employed.

EXAMPLE 4

The method of example 1 was modified; 4M instead of 8M urea was used.

EXAMPLE 5

The method of example 1 was modified; 6M instead of 8M urea was used.

EXAMPLE 6

The preparation was applied to heparin-Sepharose column, as in example 1, and the next steps of the method of example 1 were modified as follows. The column was washed with 20 column volumes of 0.1M NaCl, 8M urea, 5 mM EDTA, 25 mM phosphate buffer (pH 8.0). Vitronectin was eluted from the column with 0.5M NaCl, 8M urea, 5 mM EDTA, 25 mM phosphate buffer.

EXAMPLE 7

The method of example 6 was modified; phosphate buffer was pH 7.0.

EXAMPLE 8

The method of example 6 was modified; phosphate buffer was pH 6.0.

EXAMPLE 9

The method of example 7 was modified; 6M instead of 8M urea was used.

EXAMPLE 10

The method of example 9 was modified as follows. Instead of leaving the preparation in the presence of 6M urea at room temperature for 2 hr., the preparation was boiled in the presence of 6M urea for 5 min.

EXAMPLE 11

The method of example 7 was modified. In example 7, ethanol was so added to the preparation at 4° C. that the final concentration of ethanol became 10%. Instead, 20 mM CaCl₂ was added and the mixture was left at room temperature for 2 hr.

EXAMPLE 12

The method of example 7 was modified. In example 7, ethanol was so added at 4° C. that the final concentration of ethanol became 10%. This step was omitted.

EXAMPLE 13

The method of example 12 was modified. 1 mM of dithiothreitol was added to all solutions.

The results are shown in Table 1.

TABLE 1

| | Purity, recovery, and amount of obtained vitronectin. | | |
|---|---|---|---|
| | Purity (-fold) | Recovery (%) | Amount (mg) |
| Example 1 | 400 | 25 | 5.0 |
| Example 2 | 400 | 19 | 3.8 |
| Example 3 | 409 | 26 | 5.2 |
| Example 4 | 100 | —* | —* |
| Example 5 | 350 | 31 | 6.2 |
| Example 6 | 190 | 32 | 6.4 |
| Example 7 | 167 | 41 | 8.2 |
| Example 8 | 77 | 30 | 6.0 |
| Example 9 | —* | 34 | 6.8 |
| Example 10 | 310 | 19 | 3.8 |
| Example 11 | 103 | 20 | 4.0 |
| Example 12 | 220 | 23 | 4.6 |
| Example 13 | 360 | 15 | 3.0 |

*was not calculated.

I claim:

1. A method for recovering purified vitronectin from a biological material in which vitronectin is present, which consists essentially of contacting immobilized glycosaminoglycan with the biological material in the presence of a protein denaturing agent whereby the conformation of vitronectin present in the biological material is altered such that the binding activity of said vitronectin to glycosaminoglycan is selectivity increased whereby vitronectin binds selectively to the immobilized glycosaminoglycan and recovering the bound vitronectin.

2. The method of claim 1 wherein the glycosaminoglycan comprises heparin and the protein denaturing agent comprises urea.

3. The method of claim 1 wherein the glycosaminoglycan comprises heparin and the protein denaturing agent comprises quanidine-HCl.

4. The method of claim 1 wherein the biological material in which vitronectin is present comprises animal serum, body fluid, tissues or their processed substances.

5. The method of claim 1 wherein the biological material in which vitronectin is present comprises animal plasma.

6. The method of claim 1 wherein the biological material containing vitronectin comprises tissue-culture cells, cell culture medium or processed substances derived from tissue culture cells or cell culture medium.

7. The method of claim 2 wherein the urea is added at a concentration of from about 4 to 8 molar.

8. The method of claim 2 wherein the urea is added at a concentration of about 8M.

* * * * *